United States Patent [19]

Dick et al.

[11] Patent Number: 4,945,181
[45] Date of Patent: Jul. 31, 1990

[54] METHOD FOR RESOLUTION OF RACEMIC THIAMPHENICOL PRECURSORS AND INTERMEDIATES THEREFOR

[75] Inventors: Helmut Dick, Frankenthal; Wolf-Dietrich Gradel, Ludwigshafen-Ruchheim; Mathias Weber, Mutterstadt, all of Fed. Rep. of Germany

[73] Assignee: Boehringer Mannheim GmbH, Mannheim, Fed. Rep. of Germany

[21] Appl. No.: 936,173

[22] Filed: Dec. 1, 1986

[30] Foreign Application Priority Data

Dec. 5, 1985 [DE] Fed. Rep. of Germany ....... 3543021

[51] Int. Cl.$^5$ ............... A61K 31/10; C07C 147/10; C07C 147/12; C07C 147/14
[52] U.S. Cl. .................. 564/212; 564/273; 564/302; 564/303; 564/341; 564/360
[58] Field of Search ............. 564/212, 341, 273, 360, 564/302, 303

[56] References Cited

U.S. PATENT DOCUMENTS

| | | | |
|---|---|---|---|
| 2,726,266 | 12/1955 | Piroue | 564/212 |
| 2,742,500 | 4/1956 | Gregory et al. | 564/212 X |
| 2,791,595 | 5/1957 | Edgerton | 564/273 X |
| 4,582,918 | 4/1986 | Nagabhyshan et al. | 564/273 X |

FOREIGN PATENT DOCUMENTS

| | | | |
|---|---|---|---|
| 526865 | 6/1956 | Canada | 564/212 |
| 0014437 | 8/1980 | European Pat. Off. | 564/212 |
| 2454805 | 11/1974 | Fed. Rep. of Germany | 564/212 |
| 770277 | 3/1957 | United Kingdom | 564/212 |
| 1433977 | 4/1976 | United Kingdom | 564/212 |

OTHER PUBLICATIONS

Secor, Chem. Reviews, vol. 63, pp. 297 to 309 (1963).
Gabor et al., Chemical Abstracts, vol. 52, 1948 to 1949 (1958).
Uallonitsch et al., Chemical Abstracts, vol. 52, #20062g (1958).
Nagana et al., Chemical Abstracts, vol. 52, 307 to 308 (1958).
Rebstock et al., J. Amer. Chem. Soc., vol. 72, pp. 186 to 187 (1955).

*Primary Examiner*—Floyd D. Higel
*Attorney, Agent, or Firm*—Felfe & Lynch

[57] ABSTRACT

The present invention provides a process for the preparation of thamphenicol (I) from D,L-threo-1-(p-methylsulphonylphenyl)-2-aminopropane-1, 3-diol hydrochloride (V) and intermediates thereof. The process comprises conversion to a corresponding benzal compound followed by hydrolysis to D,L-threo-aminodiol.HCl and the following steps:

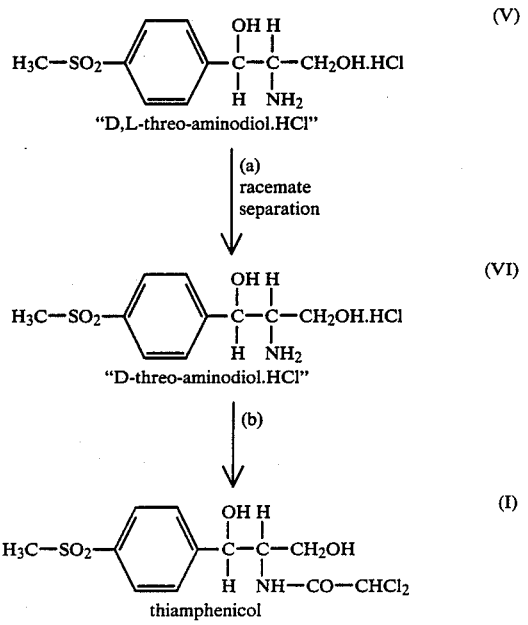

11 Claims, No Drawings

METHOD FOR RESOLUTION OF RACEMIC THIAMPHENICOL PRECURSORS AND INTERMEDIATES THEREFOR

The present invention is concerned with an improved process for the preparation of thiamphenicol, i.e. D-threo-1-(p-methylsulphonylphenyl)-2-dichloroacetamidopropane-1,3-diol, and, in particular, is concerned with the resolution of racemic thiamphenicol precursors, as well as with intermediates which can be used in this process.

Thiamphenicol is an optically-active compound, the antibacterial activity of which is about twice as great as that of the corresponding racemic compound (M. C. Rebstock and L. L. Bambas, J.A.C.S., 77, 186/1955).

D,L-threo-1-(p-methylsulphonylphenyl)-2-aminopropane-1,3-diol (D.L.threoaminodiol)(II) is an important intermediate in the synthesis of thiamphenicol (I). This intermediate can be prepared in the form of the sulphate (III) by hydrogenation of D,L-threo-1-(p-methylsulphonylphenyl)-2-nitropropane-1,3-diol (SNK) using palladium charcoal as catalyst, SNK being obtained analogously to the process described in DE-B No. 862 302 by the condensation of p-methylsulphonyl-benzaldehyde with 2-nitroethanol.

Various processes are known from the literature, also for similar compounds, for the resolution of enantiomers. Usually, the enantiomeric mixture is thereby reacted with optically-active adjuvants and the diastereomeric adducts thus produced are then resolved on the basis of their differing physical properties (cf., for example, U.S.-B No. 2,742,500). In less frequent cases, it is also possible to obtain the enantiomers directly from the racemate by selective crystallization. Thus, this has, in the meantime, been successful in the case of quite a number of compounds (cf., Chem. Reviews, 63, 297/1963). However, an application to the preparation of thiamphenicol (I) from D,L-threo-aminodiol (II) is hitherto unknown. This is obviously due to the fact, which has, in the meantime, been experimentally demonstrated, that the free base (II), in contradistinction to, for example, the corresponding free base in the case of the synthesis of chloramphenicol, cannot be brought to selective crystallization.

Therefore, it is an object of the present invention to provide a process with which the resolution of the racemate can be carried out in the thiamphenicol process which is economically and ecologically superior to the resolution with adjuvants. It is thereby an especial object to carry out this selective crystallization in its most economic form, i.e. the so-called oscillating racemate resolution. By an oscillating racemate resolution is to be understood a resolution of a racemate by an alternating selective crystallization of the enantiomers from a supersaturated solution of the racemate after seeding (cf. R. M. Secor, Resolution of optical isomers by crystallization procedures, Chem. Reviews, 63, 297/1963).

According to the present invention, this object is achieved in that (a) there is selected an intermediate suitable for the selective crystallization;
(b) there are found solvents which are especially suitable for the selective crystallization; and
(c) there is developed an economic process for the preparation of thiamphenicol from the intermediate.

In contradistinction to processes known from the literature using optically-active adjuvants, the new process according to the present invention results in a drastic reduction of the production costs since the expensive adjuvants are unnecessary and the yield is almost quantitative. Furthermore, the new process also permits the isolation of the "false" isomer (L-threo compound) and thus provides the possibility of reuse, for example renewed racemization and recycling to the resolution process.

Starting from D,L-threo-1-(p-methylsulphonyl-phenyl)-2-aminopropane-1,3-diol hydrochloride (V), which can be obtained in known manner from the sulphate (III) via the Schiffs base (IV) and hydrolysis thereof with hydrochloric acid, the racemate resolution, as well as the reaction to give the final product, proceeds according to the following scheme:

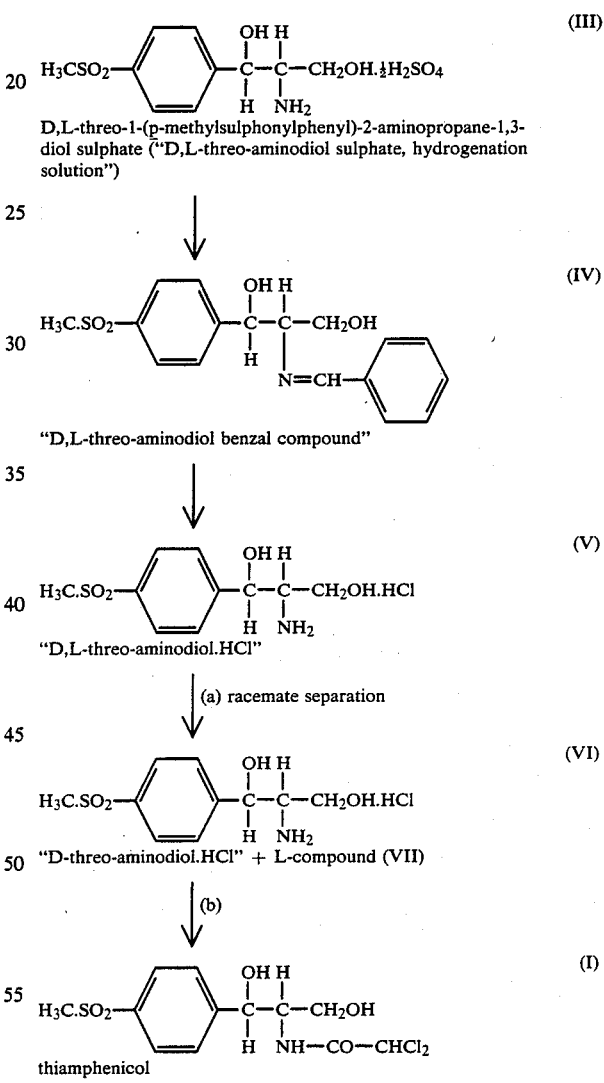

Surprisingly, it has been found that the hydrochloride (V), in contradistinction to the free base (II) and to a number of salts with inorganic and organic acids, permits, in an outstanding manner, a-selective crystallization in step (a).

The selective crystallization or preferably the oscillating racemate resolution at step (a) is preferably carried out from supersaturated solutions in mixtures of alkanol/water, alkanol/water/concentrated hydrochloric acid, water/concentrated hydrochloric acid or alkanol/hydrogen chloride in any desired mole ratios. By alkanols are preferably to be understood lower alcohols, ethanol and methanol being especially preferred. The concentration of the corresponding aminodiol.HCl compounds (V, VI, VII) in the crystallization solution varies at the crystallization temperature up to 200% supersaturation and especially preferably up to 150% supersaturation. The selective crystallization can be carried out at a temperature of from −20° C. to +80° C., the crystallization temperature preferably being from 0° to 60° C.

The further working up (step b) of the D-threo-aminodiol.HCl (VI) obtained by the enantiomer separation (cf. GB-B No. 745,900) to give thiamphenicol (I) takes place with a yield of about 96% (including recyclings) by converting the D-threo-aminodiol.HCl (VI) in methanol with sodium methylate into the free base, reacting with methyl dichloroacetate to give thiamphenicol and crystallizing the thiamphenicol from methanol/water.

The optical purity of the D-threo-aminodiol.HCl (VI) obtained in the case of the oscillating racemate resolution generally suffices for the preparation of the thiamphenicol. In exceptional cases, the content of the "false" isomer can be too high. The desired optical purity can here easily be achieved by subsequently stirring the D-threo-aminodiol.HCl from 95% alcohol or from dilute aqueous hydrochloric acid.

The following Examples are given for the purpose of illustrating the present invention:

EXAMPLE 1

900 g. D,L-threo-1-(p-methylsulphonylphenyl)-2-aminopropane-1,3-diol hydrochloride (D,L-threo-aminodiol.HCl) (V)(m.p. 172°–175° C.) and 90 g. L-threo-aminodiol.HCl ($[\alpha]_D^{20} = +26.5°$ (c=2 in water; m.p. 201°–203° C.) are dissolved, under reflux, in 4050 g. ethanol (95% denatured with 1% by volume methyl ethyl ketone), heated under reflux for 15 minutes with 20 g. active charcoal and filtered. The filtrate is adjusted with ethanol to a weight of 5040 g. (=6020 ml. at 50° C.). At 50° C., there is obtained a supersaturated alcoholic solution with the following content:
17.9% D,L-threo-aminodiol.HCl and
1.8% L-threo-aminodiol.HCl.

With slow stirring, it is seeded at 50° C. and with an initial optical rotation of the solution of $\alpha_D^{50}$ of +0.8° with 0.5 g. L-threo-aminodiol.HCl ($[\alpha]_D^{20} = +26.5°$ (c=2, water); m.p. 201°–203° C., crystal size 98% <74μ). In order to be able to observe the course and the conclusion of the crystallization, filtered samples are measured from time to time in a polarimeter ($\alpha_D^{50}$ in a 2 dm. cuvette). After a crystallization time of about 4 hours, with a final optical rotation of the filtered solution of −0.9°, it is filtered off, the crystallizate is washed with 300 ml. 95% ethanol with a temperature of 0° C. and dried at 50° C. Yield 170 g. L-threo-aminodiol.HCl (VII)($[\alpha]_D^{20} = +25.0°$ (c=2, water); m.p. 200°–202° C.). Because of the taking of samples (about 5 with measurement of $\alpha_D^{50}$) for the control of the process, the yield of active salt is less than the expected yield of about 180 g.

The wash liquid and mother liquor are combined, 180 g. D,L-threo-aminodiol.HCl are added thereto and dissolved therein, the solution is treated with charcoal and a concentration of about 17.9% of the D,L-compound and of 1.8% of the D-compound are adjusted by distillation. After seeding with 0.5 g. D-threo-aminodiol.HCl at 50° C., it is again crystallized for about 4 hours until the optical rotation of the filtered solution has increased at $\alpha_D^{50}$ to +0.9°. The crystals are filtered off with suction, washed with 300 ml. 95% ethanol and dried at 50° C. Yield: 170 g. D-threo-aminodiol.HCl (VI)($[\alpha]_D^{20} = -25.0°$ (c=2, water); m.p. 200°–202° C.). There again follows a crystallization of L-threoaminodiol.HCl (VII) and so forth.

The crystallization can be repeated frequently. Because of the impurities enriching in the mother liquor, the solubilities and thus the crystallization times also increase. In order that these remain constant, the crystallization temperature can be gradually lowered from batch to batch to about +30° C. and/or the concentration of D,L-threo-aminodiol.HCl can be gradually increased from batch to batch.

EXAMPLE 2

1800 g. D,L-threo-1-(p-methylsulphonylphenyl)-2-aminopropane-1,3-diol hydrochloride (D,L-threo-aminodiol.HCl) (V)(m.p. 172°–175° C.) and 150 g. L-threo-aminodiol.HCl ($[\alpha]_D^{20} = +26.5°$ (c=2, water); m.p. 201°–203° C.) are dissolved in 1150 ml. distilled water at 50° C. and the solution is filtered. The filtrate is mixed with 1130 g. 38% hydrochloric acid and cooled to 30° C. A supersaturated aqueous solution is obtained with the following content:
42.6% D,L-threo-aminodiol.HCl
3.5% L-threo-aminodiol.HCl
10.2% hydrogen chloride.

The optical rotation $\alpha_D^{30}$ of a sample, diluted 1:5 v/v with water and measured in a 1 dm. cuvette with a polarimeter, is +0.5°. The solution is seeded at 30° C. with 1 g. L-threo-aminodiol.HCl (crystal size 98% <74μ) and crystallized for about 6 hours, with gentle stirring, at 30° C. until the optical rotation $\alpha_D^{30}$ of a filtered sample (dilute with water 1:5 v/v) is −0.6°.

The crystals are filtered off with suction and washed portionwise with 260 ml. 95% ethanol with a temperature of 30° C. and then with 780 ml. 95% ethanol with a temperature of 0°–5° C. The crystallizate weighs 290 g. after drying at 60° C. ($[\alpha]_D^{20} = +25.5°$ (c=2, water); m.p. 201°–202° C.). Because of the sampling for the process control, the yield of active salt is less than the expected yield of about 300 g. After evaporation of the wash ethanol, there are obtained 150 g. of almost racemic aminodiol.HCl. The residue from the wash liquid is dissolved in the mother liquor of the L-crystallization, made up with 300 g. D,L-threo-aminodiol.HCl, dissolved at about 70° C. and the crystallization conditions produced as before the commencement of the L-crystallization.

After seeding with 1 g. D-threo-aminodiol.HCl (VI) at 30° C., slow stirring is again carried out for about 6 hours until the optical rotation $\alpha_D^{30}$ has increased from −0.5° to +0.6°. The D-threo-aminodiol.HCl (VI) is filtered off with suction, washed with 95% ethanol and dried at 60° C. The yield is 290 g. ($[\alpha]_D^{20} = -25.5°$ (c=2, water); m.p. 201°–202° C.). Because of the sampling for the process control, the yield of active salt is less than the expected yield of 300 g.

There then again follows a crystallization of L-threo-aminodiol.HCl (VII) and so forth.

Depending upon the purity of the D,L-threo-aminodiol.HCl (V) used, L- and D-compound can be crystallized alternatingly from the same solution up to 100 times and more. The crystallization times thereby slowly increase from batch to batch. By gradually increasing the concentration of D,L-threo-aminodiol.HCl (up to about 52%) and the concentration of hydrogen chloride up to about 12%, the crystallization times can be kept between 3 and 10 hours.

EXAMPLE 3

1168 g. D,L-threo-1-(p-methylsulphonylphenyl)-2-aminopropane-1,3-diol hydrochloride (D,L-threo-aminodiol.HCl) (V)(m.p. 172°–175° C.) and 85 g. L-threo-aminodiol.HCl ($[\alpha]_D^{20} = +26.5°$ (c=2, water); m.p. 201°–203° C.) are dissolved under reflux in a mixture of 379 g. water and 734 g. 99% ethanol, denatured with 1% by volume methyl ethyl ketone. After cooling to 25° C., there is obtained a supersaturated solution with the following content:

49.4% D,L-threo-aminodiol.HCl
3.6% L-threo-aminodiol.HCl
16.0% water
31.0% ethanol (99% denatured with 1% by volume methyl ethyl ketone).

The optical rotation $\alpha_D^{25}$ of a sample, measured in a 1 dm cuvette with a polarimeter, is +1.2°. At 25° C., seeding is carried out with 1 g. L-threo-aminodiol.HCl (crystal size 98% <74μ) and crystallization is carried out for about 6 hours, with gentle stirring, at 25° C. until the optical rotation $\alpha_D^{25}$ of a filtered sample is −1.3°.

The crystals are filtered off with suction and washed portionwise once with 260 ml. 95% denatured ethanol with a temperature of 40° C. and three times with 260 ml. amounts of 95% denatured ethanol with a temperature of 0°–5° C. After drying at 60° C., the crystallizate (L-threo-aminodiol.HCl)(VII) weighs 160 g. ($[\alpha]_D^{20} = +25.3°$ (c=2, water); m.p. 200.5°–201.5° C.). Because of the sampling for the process control, the yield of active salt is less than the expected yield of about 170 g.

After evaporation of the wash ethanol, there are obtained 190 g. of almost racemic aminodiol.HCl. The residue from the wash liquid is dissolved in the mother liquor of the L-crystallization, made up with 170 g. D,L-threo-aminodiol.HCl, dissolved under reflux and the crystallization conditions produced as before commencement of the L-crystallization by the addition of ethanol and water. After seeding with 1 g. D-threo-aminodiol.HCl (VI) at 25° C., slow stirring is again carried out for about 6 hours until the optical rotation $\alpha_D^{25}$ has increased from −1.2° to +1.3°. The crystals are filtered off with suction, washed with 95% ethanol as described above and the D-threo-aminodiol.HCl (VI) obtained is dried at 60° C. Yield 160 g. ($[\alpha]_D^{20} = -25.5°$ (c=2, water); m.p. 201°–202° C.). Because of the sampling for the process control, the yield of active salt is less than the expected yield of about 170 g.

The again follows a crystallization of L-threo-aminodiol.HCl (VII) and so forth.

In the final step of converting D-threo-aminodiol.HCl to thiamphenicol, the reactants, and especially sodium methylate, are quite aggressive. Thus, in the preferred manner of carrying out the step of preparing thiamphenicol from D-threo-aminodiol.HCl with sodium methylate and methyl dichloroacetate in methanol, the reaction is carried out in a stainless steel vessel with the addition of the tetrasodium salt of ethylenediamine-tetraacetic acid in an amount of 0.001% to 10% related to D-threo-aminodiol.HCl, 0.1% to 1% being especially preferred.

It will be understood that the specification and examples are illustrative but not limitative of the present invention and that other embodiments within the spirit and scope of the invention will suggest themselves to those skilled in the art.

What is claimed is:

1. A process for the preparation of thiamphenicol from D,L-threo-1-(p-methylsulphonylphenyl)-2-aminopropane-1,3-diol hydrochloride which is first converted to D,L-threo-aminodiolbenzal comprising
   hydrolyzing the D,L-threo-aminodiolbenzal to D,L-threo-aminodiol.HCl;
   separating D-threo-aminodiol.HCl from the D,L-threoaminodiol.HCl by selective crystallization by oscillating racemate resolution comprising alternating crystallization of D-Threo-aminodiol.HCl and of L-threo-aminodiol.HCl; and
   converting D-threo-aminodiol.HCl to thiamphenicol.

2. The process of claim 1 wherein D-threo-aminodiol.HCl is selectively crystallized by seeding a solution supersaturated with up to 200% D,L-threo-aminodiol.HCl with D-threo-aminodiol.HCl, the solution solvent being selected from the group consisting of a $C_1$–$C_6$ lower alcohol, a $C_1$–$C_6$ lower alcohol with the addition of hydrogen chloride, a mixture of a $C_1$–$C_6$ lower alcohol and water, a mixture of a $C_1$–$C_6$ lower alcohol and water with the addition of concentrated hydrocholoric acid and aqueous hydrochloric acid, and crystallizing the D-threo-aminodiol.HCl from the solution at a temperature from about −20° to about +80° C.

3. The process of claim 2 wherein L-threo-aminodiol.HCl is selectively crystallized by seeding a solution supersaturated with up to 200% D,L-threo-aminodiol.HCl with L-threo-aminodiol.HCl, the solution solvent being selected from the group consisting of a $C_1$–$C_6$ lower alcohol, a $C_1$–$C_6$ lower alcohol with the addition of hydrogen chloride, a mixture of a $C_1$–$C_6$ lower alcohol and water, a mixture of a $C_1$–$C_6$ lower alcohol and water with the addition of concentrated hydrochloric acid and aqueous hydrochloric acid, and crystallizing the L-threo-aminodiol.HCl from the solution at a temperature from about −20° to about +80° C.

4. The process of claim 1 wherein L-threo-aminodiol.HCl is selectively crystallized by seeding a solution supersaturated with up to 200% D,L-threo-aminodiol.HCl with L-threo-aminodiol.HCl, the solution solvent being selected from the group consisting of a $C_1$–$C_6$ lower alcohol, a $C_1$–$C_6$ lower alcohol with the addition of hydrogen chloride, a mixture of a $C_1$–$C_6$ lower alcohol and water a mixture of a $C_1$–$C_6$ lower alcohol and water with the addition of concentrated hydrochloric acid and aqueous hydrochloric acid, and crystallizing the L-threo-aminodiol.HCl from the solution at a temperature from about −20° to about +80° C.

5. The process of claim 1 wherein the crystallized D-threoaminodiol.HCl is further freed of contamination with the L-compound by recrystallization from the solution solvent selected from the group consisting of an alcohol, an alcohol-water mixture, an alcohol containing concentrated hydrochloric acid, an alcohol-water mixture containing concentrated hydrochloric acid, and aqueous hydrochloric acid.

6. The process of claim 1 wherein thiamphenicol is formed from D-threoaminodiol.HCl by reaction with sodium methylate and methyl dichloroacetate in methanol.

7. A process for the preparation of D-threo-aminodiol.HCl from D,L-threo-aminol.HCl (V) by seeding a supersaturated solution of up to 200% D,L-threo-aminodiol.HCl, with D-threo-aminodiol.HCl, the solution solvent being selected from the group consisting of a $C_1$–$C_6$ lower alcohol, a $C_1$–$C_6$ lower alcohol with the addition of concentrated hydrochloric acid and aqueous hydrochloric acid, and selectively crystallizing the D-threo-aminodiol.HCl by oscillating racemate resolution at a temperature from about $-20°$ to about $+80°$ C.

8. The process of claim 7 further comprising purifying the D-threo-aminodiol.HCl crystals by washing with or recrystallizing from the solution solvent selected from the group consisting of an alcohol, an alcohol-water mixture, an alcohol-water mixture containing hydrochloric acid and aqueous hydrochloric acid.

9. A process for the preparation of D-threo-aminodiol.HCl from D,L-threo-aminol.HCl (V) by seeding a supersaturated solution of up to 200% D,L-threo-aminodiol.HCl, with D-threo-aminodiol.HCl, the solution solvent being selected from the group consisting of a $C_1$–$C_6$ lower alcohol, a $C_1$–$C_6$ lower alcohol with the addition of concentrated hydrochloric acid and aqueous hydrochloric acid, and selectively crystallizing the D-threo-aminodiol.HCl by oscillating racemate resolution at a temperature from about $-20°$ to about $+80°$ C.

10. The process of claim 9 further comprising purifying the L-threo-aminodiol.HCl crystals by washing with or recrystallization from a solution solvent selected from the group consisting of an alcohol, an alcohol water mixture, an alcohol-water mixture containing hydrochloric acid and aqueous hydrochloric acid.

11. A process for the preparation of thiamphenicol from D,L-threo-1-(p-methylsuphonylphenyl)-2-aminopropane-1,3-diol hydrochloride which is first converted to D,L-threo-aminodiolbenzal comprising hydrolyzing the D,L-threo-aminodiol benzal to D,L-threo-aminodiol.HCl;

separating D-threo-aminodiol.HCl from the D,L-threo-aminodiol.HCl by selective crystallization by oscillating racemate resolution comprising alternating crystallization of D-threo-aminodiol.HCl and L-threo-aminodiol.HCl; and converting D-threo-aminodiol.HCl to thiamphenicol by reaction with sodium methylate and methyl dichloroacetate in methanol in a stainless steel vessel and wherein the reaction further comprises adding the tetrasodium salt of ethylenediamine-tetracetic acid.

* * * * *